US012201611B2

(12) United States Patent
Singh et al.

(10) Patent No.: US 12,201,611 B2
(45) Date of Patent: Jan. 21, 2025

(54) COMPOSITION COMPRISING HIGH PURITY PYRROLE DERIVATIVE AND METHOD FOR PREPARATION THEREOF

(71) Applicant: Zydus Lifesciences Limited, Gujarat (IN)

(72) Inventors: Kumar Kamlesh Singh, Gujarat (IN); Sanjay Jagdish Desai, Gujarat (IN); Piyush Rajendra Sharma, Gujarat (IN); Daya Ram Pal, Gujarat (IN); Sanjeev Kumar Tripathi, Gujarat (IN); Mayur Ramnikbhai Patel, Gujarat (IN)

(73) Assignee: Zydus Lifesciences Limited, Gujarat (IN)

( * ) Notice: Subject to any disclaimer, the term of this patent is extended or adjusted under 35 U.S.C. 154(b) by 36 days.

(21) Appl. No.: 17/383,930

(22) Filed: Jul. 23, 2021

(65) Prior Publication Data

US 2022/0023262 A1    Jan. 27, 2022

(30) Foreign Application Priority Data

Jul. 24, 2020 (IN) .............................. 202021031686

(51) Int. Cl.
*A61K 31/4025* (2006.01)
*A61K 31/336* (2006.01)

(52) U.S. Cl.
CPC ........ *A61K 31/4025* (2013.01); *A61K 31/336* (2013.01)

(58) Field of Classification Search
CPC ................................................. A61K 31/4025
See application file for complete search history.

(56) References Cited

U.S. PATENT DOCUMENTS

| | | | |
|---|---|---|---|
| 6,987,123 B2 | 1/2006 | Lohray et al. | |
| 7,041,837 B2 | 5/2006 | Lohray et al. | |
| 7,323,491 B2 | 1/2008 | Lohray et al. | |
| 8,110,598 B2 | 2/2012 | Lohray et al. | |
| 8,212,057 B2 | 7/2012 | Lohray et al. | |
| 10,385,017 B2 * | 8/2019 | Desai ........................ A61P 3/06 |

FOREIGN PATENT DOCUMENTS

| | | | | |
|---|---|---|---|---|
| IN | 201921010391 A * | 1/2021 | | |
| WO | WO-2012/104869 A1 | 8/2012 | | |
| WO | WO-2014/195967 A2 | 12/2014 | | |
| WO | WO-2015029066 A1 * | 3/2015 | ................ A61P 3/06 |
| WO | WO-2015033357 A2 * | 3/2015 | ........... C07D 207/32 |
| WO | WO-2017064635 A2 * | 4/2017 | ............. A61K 31/40 |

OTHER PUBLICATIONS

Compound Registry Numbers (Year: 2023).*
Jadhav et al. (2014) "Drug Impurity Profiling: A Scientific Approach," Journal of Pharmacy Research 8(6):696-706.

* cited by examiner

*Primary Examiner* — Andrew D Kosar
*Assistant Examiner* — Gillian A Hutter
(74) *Attorney, Agent, or Firm* — Goodwin Procter LLP

(57) ABSTRACT

The present invention relates to a composition comprising high purity pyrrole derivative and method for preparation thereof. The present invention particularly relates to compositions comprising Saroglitazar magnesium having purity of 99.0% or more, and one or more of an aldehyde compound of Formula (II), diketo oxirane compound of Formula (III), hydroxy methyl compound of Formula (IV) or dimer compound of Formula (V), relative to saroglitazar magnesium, each present in an amount of about 0.15% or less, respectively, by weight, when measured by area percentage of HPLC.

12 Claims, No Drawings

COMPOSITION COMPRISING HIGH PURITY PYRROLE DERIVATIVE AND METHOD FOR PREPARATION THEREOF

This application claims priority to IN patent application Ser. No. 202021031686 filed 24 Jul. 2020, the entire contents of which is hereby incorporated by reference.

FIELD OF THE INVENTION

The present invention relates to the field of pharmaceuticals, in particular, to composition comprising high purity pyrrole derivative and method for preparation thereof. More particularly, the present invention relates to compositions comprising Saroglitazar magnesium having purity of 99.0% or more, and one or more of an aldehyde compound of Formula (II), diketo oxirane compound of Formula (III), hydroxy methyl compound of Formula (IV) or dimer compound of Formula (V), relative to saroglitazar magnesium, each present in an amount of about 0.15% or less, respectively, by weight, when measured by area percentage of HPLC.

BACKGROUND OF THE INVENTION

The following discussion of the prior art is intended to present the invention in an appropriate technical context. The pyrrole derivative of present invention is chemically 2-ethoxy-3-(4-(2-(2-methyl-5-(4-(methylthio)phenyl)-1H-pyrrol-1-yl)ethoxy)phenyl)propanoate, which is also known as Saroglitazar, and which is marketed as its magnesium salt of Formula (I),

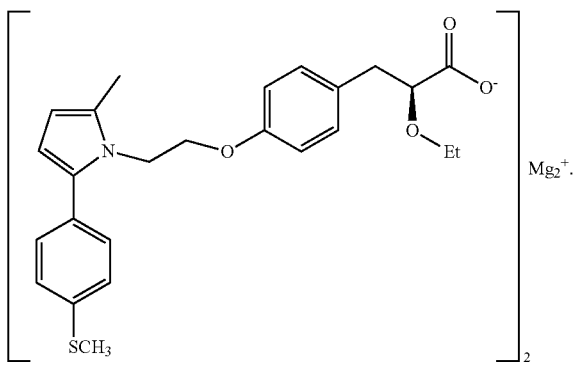

U.S. Pat. Nos. 6,987,123 B2, 7,041,837 B2, 7,323,491 B2, 8,110,598 B2, and 8,212,057 B2 discloses pyrrole derivatives their preparation, pharmaceutical compositions containing them and use thereof.

International (PCT) Publication No. WO 2012/104869 discloses the use of compound of Formula (I) for the treatment of lipodystrophy.

International (PCT) Publication Nos. WO 2014/195967, WO 2015/029066 and WO 2015/033357 disclose processes for the preparation of saroglitazar and its pharmaceutically acceptable salts thereof.

In a pharmaceutical product, an impurity is first and foremost, a quality issue, since it could potentially compromise the efficacy of the drug product. Secondly, impurities also cause safety concerns. Therefore, the objective is to know the plausible impurities for allowing assessment of their toxicological implications and for understanding their formation mechanisms, which is an important knowledge for improving the synthetic chemical pathway and optimizing the formulation. In view of the above, it is therefore desirable to provide a composition comprising saroglitazar or magnesium salt thereof having higher purity and is substantially free from one or more impurities, which could plausibly affect the safety and efficacy of the drug product.

SUMMARY OF THE INVENTION

The present invention relates to a composition comprising Saroglitazar magnesium having a purity of about 99.0% or more, and one or more of an aldehyde compound of Formula (II), or a diketo oxirane compound of Formula (III), or a hydroxy methyl compound of Formula (IV), or a dimer compound of Formula (V), each present in an amount of about 0.15%, or less, relative to Saroglitazar magnesium, by weight, when measured by area percentage of HPLC.

In one general aspect, there is provided a composition comprising Saroglitazar magnesium having a purity of about 99.0% or more, and an aldehyde compound of Formula (II) of about 0.15% or less, relative to Saroglitazar magnesium, by weight, when measured by area percentage of HPLC.

The aldehyde compound is represented by the structure of Formula (II),

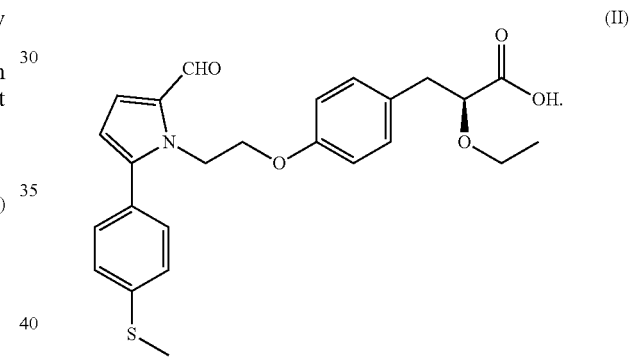

In another general aspect, there is provided a composition comprising Saroglitazar magnesium having a purity of about 99.0% or more, and a diketo oxirane compound of Formula (III), of about 0.15% or less, relative to Saroglitazar magnesium, by weight, when measured by area percentage of HPLC.

The diketo oxirane compound is represented by the structure of Formula (III),

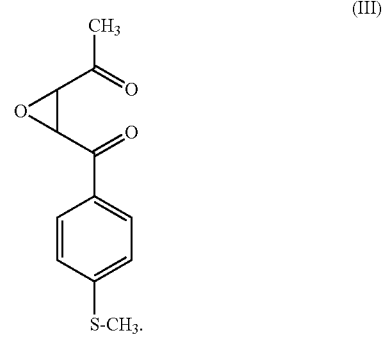

In another general aspect, there is provided a composition comprising Saroglitazar magnesium having a purity of about 99.0% or more, and hydroxy methyl compound of Formula (IV) of about 0.15% or less, relative to Saroglitazar magnesium, by weight, when measured by area percentage of HPLC.

The hydroxymethyl compound is represented by the structure of Formula (IV),

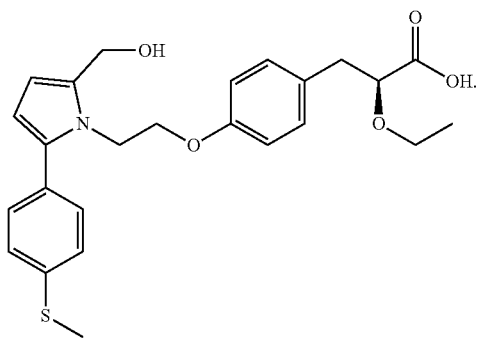

(IV)

In another general aspect, there is provided a composition comprising Saroglitazar magnesium having a purity of about 99.0% or more, and dimer compound of Formula (V) of about 0.15% or less, relative to Saroglitazar magnesium, by weight, when measured by area percentage of HPLC.

The dimer compound is represented by the structure of Formula (V),

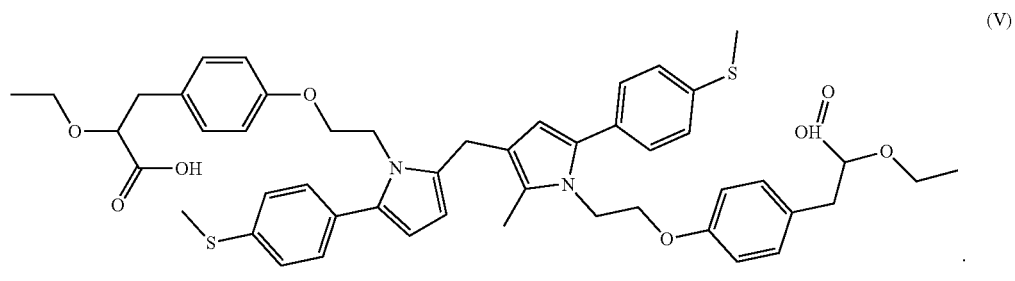

(V)

In another general aspect, there is provided a stable composition of Saroglitazar magnesium, wherein the compounds of Formula (II), Formula (III), Formula (IV), and Formula (V) remain within the permissible limits up on prolonged storage under different storage conditions.

In another general aspect, there is provided a process for the preparation of compound of Formula (3A),

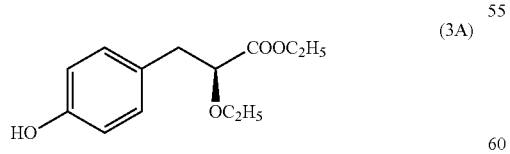

(3A)

the process comprising:
(a) reacting a compound of Formula (1A) with diethyl sulphate in one or more solvents in the presence of a base and a phase transfer catalyst to obtain a compound of Formula (2A), having diethyl sulphate content less than 5 ppm; and

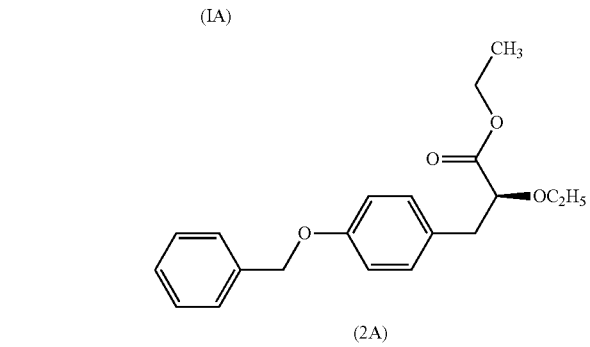

(IA)

(2A)

(b) converting the compound of Formula (2A) to the compound of Formula (3A) in the presence of a hydrogenation catalyst, at a temperature between 40° C. to 60° C.

In another general aspect, there is provided a process for the preparation of compound of Formula (2B),

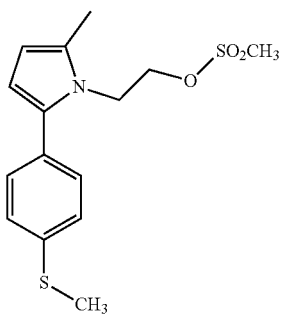

(2B)

the process comprising:
(a) reacting a compound of Formula (1B) with methyl sulphonyl chloride in one or more solvents in the presence of a base to obtain a compound of Formula (2B); and (1B)

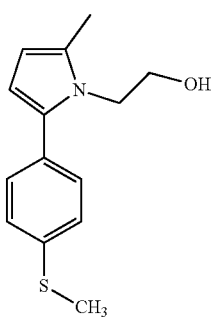

(b) obtaining the compound of Formula (2B) by addition of water while maintaining the reaction mixture at a temperature of about 0-10° C.

In another general aspect, there is provided a process for the preparation of substantially pure Saroglitazar magnesium, the process comprising:

(a) reacting a hydroxy compound (3A) with a mesylate compound (2B) in a mixture of solvents in the presence of a base to obtain an alkoxy ester compound of Formula (VI);

(3A)

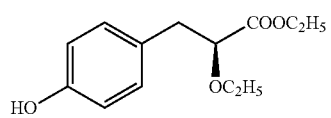

(2B)

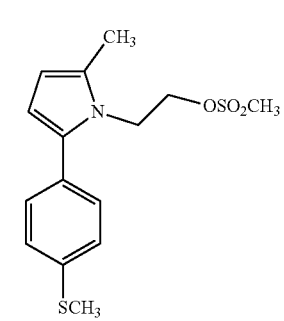

(VI)

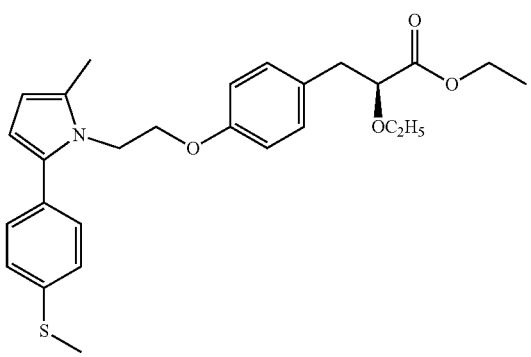

(b) hydrolyzing the alkoxy ester compound of Formula (VI) with a base in one or more solvents at a lower temperature to obtain a reaction mixture;
(c) optionally, washing the reaction mixture with one or more solvents to obtain an aqueous layer;
(d) treating the aqueous layer with one or more solvents and adjusting pH 2.0 to 6.0;
(e) extracting the aqueous layer with one or more solvents to obtain an organic layer;
(f) treating the organic layer with S-(−)-α-methylbenzyl amine to obtain saroglitazar S-(−)-α-methylbenzyl amine (SMBA) salt of Formula (VII);

(VII)

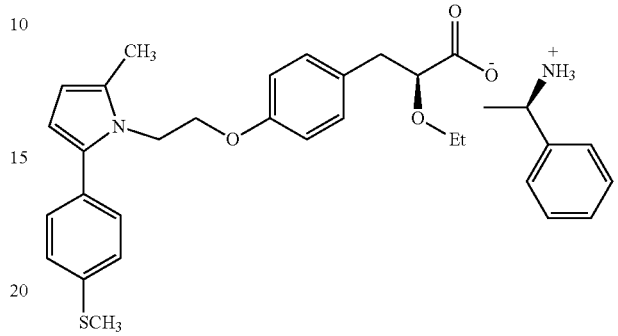

(g) purifying the saroglitazar SMBA salt with one or more solvents to obtain pure saroglitazar SMBA salt; and
(h) treating the pure saroglitazar SMBA salt with magnesium source to obtain the substantially pure saroglitazar magnesium.

The details of one or more embodiments of the invention are set forth in the accompanying description.

DETAILED DISCUSSION OF THE INVENTION

The invention provides substantially pure saroglitazar magnesium suitable for development of finished formulations, which exhibit better control of impurities and stability under various stress conditions.

The term "substantially pure" herein means Saroglitazar magnesium having a purity of 99% or more, by weight, and one or more of an aldehyde compound of Formula (II), or a diketo oxirane compound of Formula (III), or a hydroxy methyl compound of Formula (IV), or a dimer compound of Formula (V), each present in an amount within the permissible ICH limits suitable for pharmaceutical preparations. For example, but not limited to about 0.15% or less, to about 0.1% or less, or more particularly to about 0.05% or less, or most particularly not in detectable amount, by weight, when measured by area percentage of HPLC relative to Saroglitazar magnesium.

As used herein, the phrase "not in detectable amount", refers to the level of impurity in the product, which is below the level of detection limit, when analyzed using the HPLC method.

All ranges recited herein include the endpoints, including those that recite the range "between" two values. Terms such as "about", "generally", "substantially" and the like are to be construed as modifying a term or value such that it is not an absolute. This includes, at very least, the degree of expected experimental error, technique error and instrument error for a given technique used to measure a value.

As used herein, the term "obtaining" means isolating by way of filtration, filtration under vacuum, centrifugation or decantation.

As used herein, the term "composition" used herein means a physical mixture of two or more components.

As used herein, the term "pharmaceutically acceptable" means that which is useful in preparing a pharmaceutical composition that is generally non-toxic and is not biologically undesirable, and includes that which is acceptable for veterinary use and/or human pharmaceutical use.

As used herein, the term "pharmaceutical composition" is intended to encompass a drug product including the active ingredient(s), pharmaceutically acceptable excipients that make up the carrier, as well as any product which results, directly or indirectly, from combination, complexation or aggregation of any two or more of the ingredients. Accordingly, the pharmaceutical compositions encompass any composition made by admixing the active ingredient, active ingredient dispersion or composite, additional active ingredient(s), and pharmaceutically acceptable excipients.

As used herein, the term "prolonged storage" refers to storage for up to 6 months and different stability conditions refers to storage at 25° C. temperature and 60% relative humidity; or at 40° C. temperature and 75% relative humidity.

In one general aspect, there is provided a composition comprising Saroglitazar magnesium having a purity of about 99.0% or more, and one or more of an aldehyde compound of Formula (II), or a diketo oxirane compound of Formula (III), or a hydroxy methyl compound of Formula (IV), or a dimer compound of Formula (V), each present in an amount of about 0.15%, or less, relative to Saroglitazar magnesium, by weight, when measured by area percentage of HPLC.

One of the potential oxidative degradation impurity in saroglitazar is the aldehyde compound of Formula (II). The present invention provides a composition comprising Saroglitazar magnesium having a purity of about 99% or more, by weight, and the aldehyde compound of Formula (II) present in an amount relative to Saroglitazar magnesium of about 0.15% or less, by weight, when measured by area percentage of HPLC, and which is well within the standard permissible limits of impurities as per the ICH.

In one general aspect, there is provided a composition comprising Saroglitazar magnesium having a purity of about 99.0% or more, and an aldehyde compound of Formula (II) of about 0.15% or less, relative to Saroglitazar magnesium, by weight, when measured by area percentage of HPLC.

The aldehyde compound is represented by the structure of Formula (II),

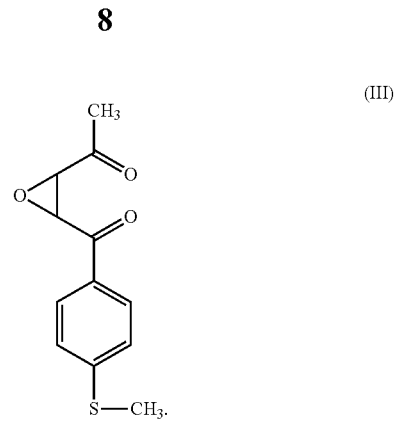

(III)

In general, the potential genesis of diketo oxirane impurity is shown below:

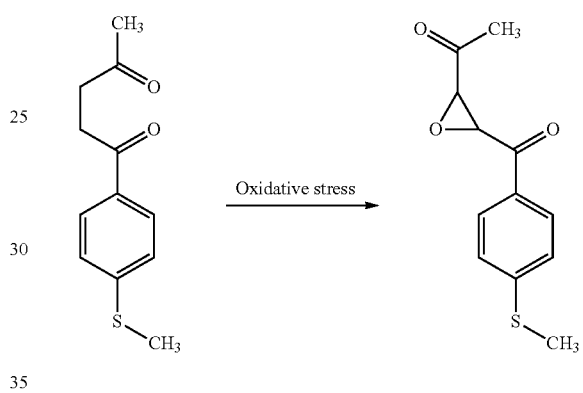

The compound 1-[4-(methylsulfanyl)phenyl]pentane-1,4-dione is one of the intermediate compound during the preparation of compound of Formula (2B).

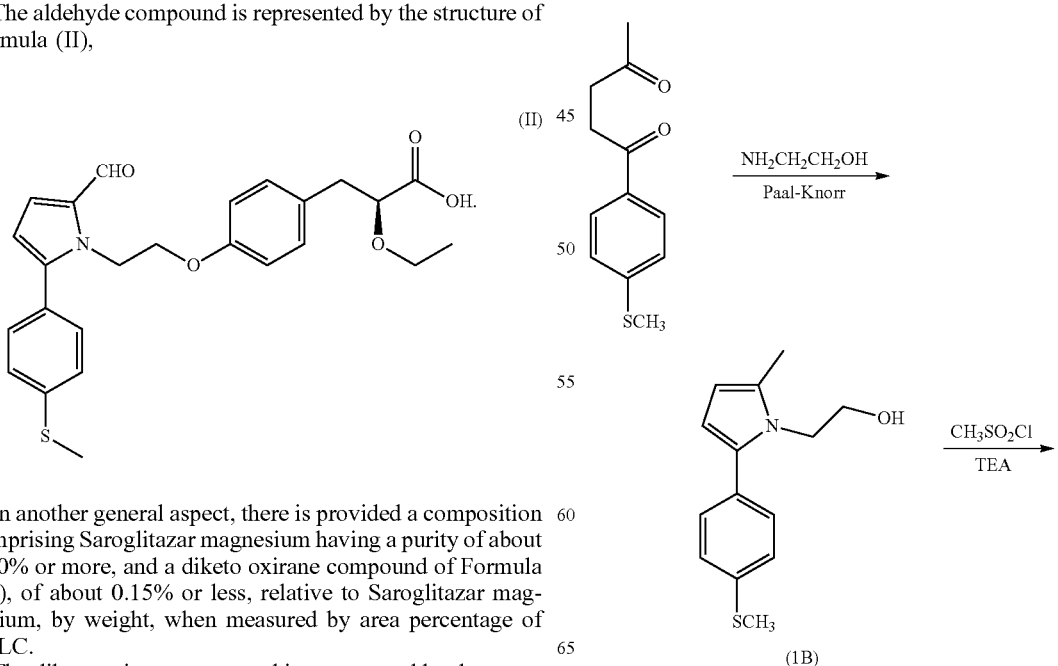

In another general aspect, there is provided a composition comprising Saroglitazar magnesium having a purity of about 99.0% or more, and a diketo oxirane compound of Formula (III), of about 0.15% or less, relative to Saroglitazar magnesium, by weight, when measured by area percentage of HPLC.

The diketo oxirane compound is represented by the structure of Formula (III),

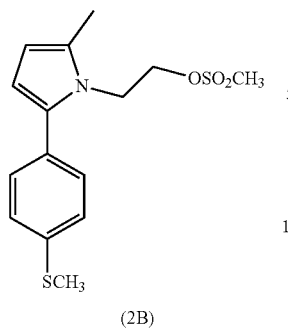

(2B)

The diketo oxirane impurity, as evident from above, is one of the potential impurities, whose genesis can be attributed to the manufacturing process of compound (2B).

In another general aspect, there is provided a composition comprising Saroglitazar magnesium having a purity of about 99.0% or more, and hydroxy methyl compound of Formula (IV) of about 0.15% or less, relative to Saroglitazar magnesium, by weight, when measured by area percentage of HPLC.

The hydroxymethyl compound is represented by the structure of Formula (IV),

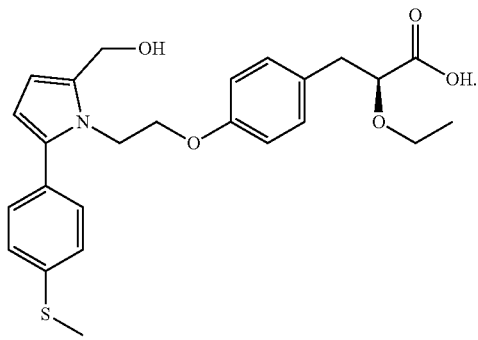

(IV)

In another general aspect, there is provided a composition comprising Saroglitazar magnesium having a purity of about 99.0% or more, and dimer compound of Formula (V) of about 0.15% or less, relative to Saroglitazar magnesium, by weight, when measured by area percentage of HPLC.

The dimer compound of Formula (V) is a process related impurity which is formed during the manufacturing process of Saroglitazar magnesium. The precursor for the formation of dimer impurity (compound of Formula (V)) is the dimer of compound of Formula (2B) which represented by the compound of Formula (3C),

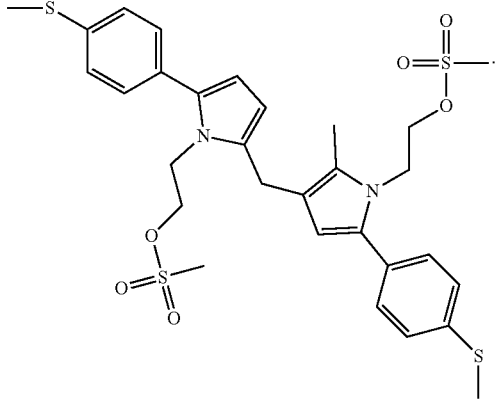

(3C)

The formation of compound of Formula (3C) is controlled by the reaction and isolation conditions employed for the preparation of compound of Formula (2B).

In another general aspect, there is provided an aldehyde compound of Formula (II),

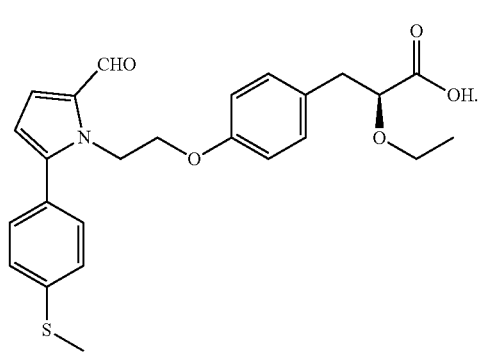

(II)

In another general aspect, there is provided a diketo oxirane compound of Formula (III),

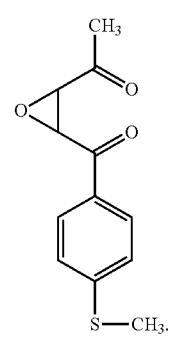

(III)

In another general aspect, there is provided a hydroxymethyl compound of Formula (IV),

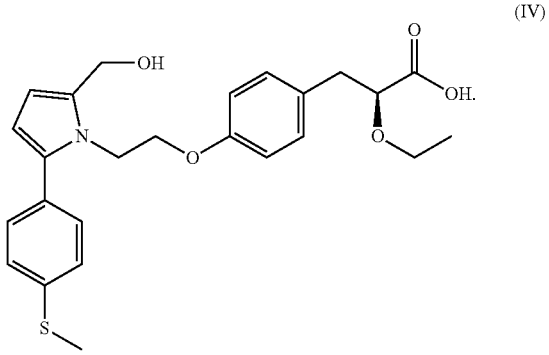 [SMILES: CCO[C@@H](Cc1ccc(OCCn2c(CO)ccc2-c2ccc(SC)cc2)cc1)C(=O)O]

In another general aspect, there is provided a process for the preparation of compound of Formula (3A),

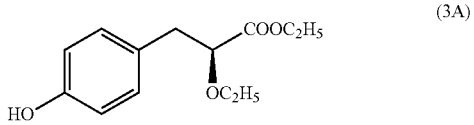

the process comprising:
(a) reacting a compound of Formula (1A) with diethyl sulphate in one or more solvents in the presence of a base and a phase transfer catalyst to obtain a compound of Formula (2A), having diethyl sulphate content less than 5 ppm; and

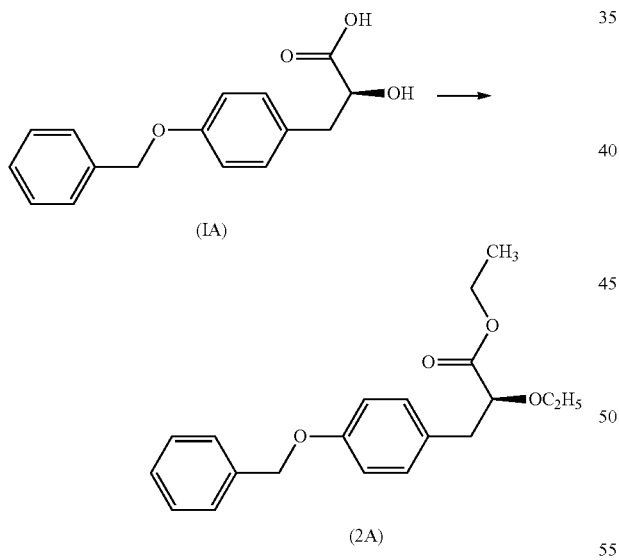

(b) converting the compound of Formula (2A) to the compound of Formula (3A) in the presence of a hydrogenation catalyst, at a temperature between 40° C. to 60° C.

In general, the diethyl sulphate is toxic substance as well as a carcinogen. The objective of the process is to provide compound of Formula (3A) having diethyl sulphate content of about 5 ppm or less.

In general, the organic solvent comprises one or more of esters selected from ethyl acetate, isopropyl acetate, t-butyl acetate, and isobutyl acetate; hydrocarbons selected from toluene, xylene, ethyl benzene, heptane, hexane, and cyclohexane; and chlorinated solvents selected from methylene dichloride, ethylene dichloride, chlorobenzene, chloroform, and carbon tetrachloride. In particular toluene can be used.

In general, the base at step (a) is selected from a group comprising sodium hydroxide, potassium hydroxide, lithium hydroxide, calcium hydroxide, sodium carbonate, potassium carbonate, sodium bicarbonate, potassium bicarbonate, sodium hydroxide, potassium hydride, sodium methoxide, potassium tert-butoxide, and sodium pentoxide. In particular, potassium methoxide can be used.

In general, the phase transfer catalyst at step (a) is selected from a group comprising tetrabutyl ammonium bromide (TBAB), tetrabutyl ammonium iodide (TBAI), benzyl triethyl ammonium chloride (TEBAC), polyethylene Glycol (PEG-200, 400, 600, 800, 1000), crown ethers selected from 12-crown-4, 15-crown-5, 18-crown-6, dibenzo-18-crown-6, and diaza-18-crown-6. In particular, the phase transfer catalyst can be TBAB.

In general, the hydrogenation catalyst at step (b) is selected from palladium, platinum or Raney nickel.

In another general aspect, there is provided a process for the preparation of compound of Formula (2B),

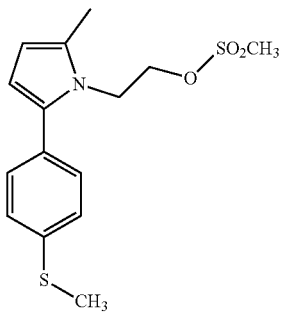

the process comprising:
(a) reacting a compound of Formula (1B) with methyl sulphonyl chloride in one or more solvents in the presence of a base to obtain a compound of Formula (2B); and

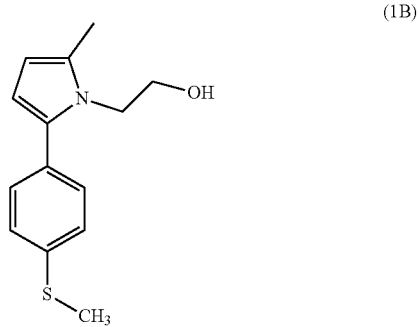 [SMILES: CSc1ccc(-c2ccc(C)n2CCO)cc1]

(b) obtaining the compound of Formula (2B) by addition of water while maintaining the reaction mixture at a temperature of about 0-10° C.

In general, the organic solvent comprises one or more of esters selected from ethyl acetate, isopropyl acetate, t-butyl acetate, and isobutyl acetate; hydrocarbons selected from toluene, xylene, ethyl benzene, heptane, hexane, and cyclohexane; chlorinated solvents selected from methylene dichloride, ethylene dichloride, chlorobenzene, chloroform, and carbon tetrachloride. In particular toluene can be used.

In general, the base at step (a) comprises one or more of alkali metal hydroxides selected from sodium hydroxide, potassium hydroxide, and lithium hydroxide; alkali metal carbonates selected from sodium carbonate, potassium carbonate, and cesium carbonate; alkali metal bicarbonates selected from sodium bicarbonate, and potassium bicarbonate; ammonia or its aqueous solution; organic bases selected from methyl amine, ethyl amine, triethylamine, tert-butyl amine, diisopropyl amine, diisopropyl ethyl amine, pyridine, piperidine, morpholine, 1,8-diazabicyclo[5.4.0]undec-7-ene, 1,4-diazabicyclo[2.2.2]octane, and 1,5-diazabicyclo[4.3.0]non-5-ene. In particular, triethylamine may be used.

In another general aspect, there is provided a process for the preparation of composition comprising substantially pure saroglitazar magnesium having a purity of about 99.0% or more, by weight, when measured by area percentage of HPLC, the process comprising:

(a) reacting a hydroxy compound (3A) with a mesylate compound (2B) in mixture of solvents in the presence of a base to obtain an alkoxy ester compound of Formula (VI);

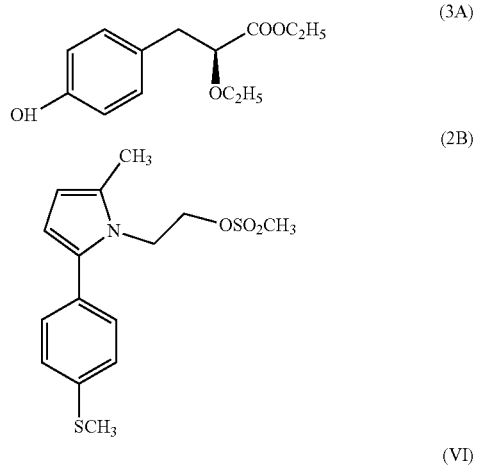

(3A)

(2B)

(VI)

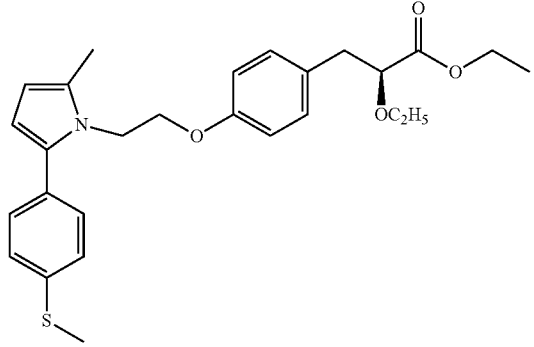

(b) hydrolyzing the alkoxy ester compound of Formula (VI) with a base in one or more solvents at a lower temperature to obtain a reaction mixture;
(c) optionally, washing the reaction mixture with one or more solvents to obtain an aqueous layer;
(d) adjusting pH of the aqueous layer to 2.0 to 6.0;
(e) extracting the aqueous layer with one or more organic solvents to obtain an organic layer;

(f) treating the organic layer with S-(−)-α-methylbenzyl amine to obtain saroglitazar S-(−)-α-methylbenzyl amine (SMBA) salt of Formula (VII);

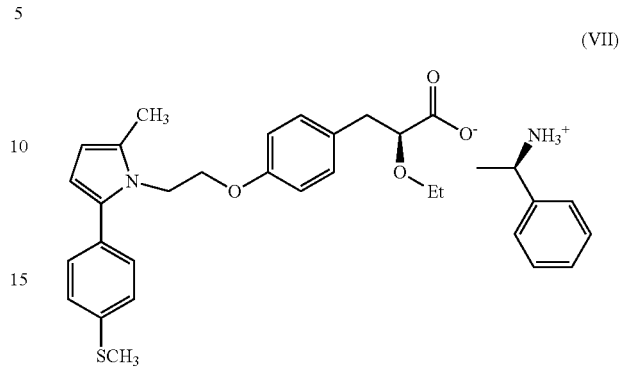

(VII)

(g) purifying the saroglitazar SMBA salt with one or more solvents to obtain pure saroglitazar SMBA salt; and
(h) treating the pure saroglitazar SMBA salt with magnesium source to obtain the substantially pure saroglitazar magnesium.

In general, the solvent comprises one or more of alcohols selected from methanol, ethanol, isopropanol, 2-propanol, 1-butanol, and t-butyl alcohol; ketones selected from acetone, butanone, and methyl isobutyl ketone; esters selected from ethyl acetate, isopropyl acetate, t-butyl acetate, and isobutyl acetate; chlorinated hydrocarbons selected from methylene dichloride, ethylene dichloride, and chlorobenzene; hydrocarbons selected from pentane, hexane, heptane, and cyclohexane; ethers selected from tetrahydrofuran, 1,4-dioxane, diisopropyl ether, diethyl ether, and methyl tert-butyl ether; or mixture thereof. In particular, the mixture of cyclohexane and tetrahydrofuran may be used.

In general, the base comprises one or more of sodium hydroxide, potassium hydroxide, lithium hydroxide, calcium hydroxide, sodium carbonate, potassium carbonate, sodium bicarbonate, potassium bicarbonate, sodium hydride, potassium hydride, potassium tert-butoxide, and sodium pentoxide. In particular, potassium carbonate is used. The base may be preferably anhydrous.

Optionally, the reaction may be catalyzed by a phase transfer catalyst. The phase transfer catalyst comprises one or more of tetrabutyl ammonium bromide (TBAB), tetrabutyl ammonium iodide (TBAI), benzyl triethyl ammonium chloride (TEBAC), polyethylene glycol (PEG-200, 400, 600, 800, 1000), crown ethers like 12-crown-4, 15-crown-5, 18-crown-6, dibenzo-18-crown-6, and diaza-18-crown-6. In particular, the phase transfer catalyst may be 18-crown-6.

In general, the reaction of a hydroxy compound (3A) and a mesylate compound (2B) may be performed under heating at 35° C. to about reflux temperature of solvents. In particular, the reaction may be heated at 75° C. to 85° C. till the completion of the reaction. The reaction may be heated for about 35 hours to about 50 hours. Particularly for about 48 hours.

In another general aspect the obtained alkoxy ester (VI) may be preceded further without isolating. Therefore, the alkoxy ester (VI) may be further hydrolyzed in-situ.

The base for hydrolyzing the alkoxy ester (VI) comprises one or more of sodium hydroxide, potassium hydroxide, lithium hydroxide, calcium hydroxide, sodium carbonate, potassium carbonate, sodium bicarbonate, potassium bicarbonate, sodium hydride, potassium hydride, potassium tert-butoxide, and sodium pentoxide. In particular, sodium hydroxide may be used.

In general, the hydrolysis of the alkoxy ester at above room temperature results in increase of dimer impurity and sulfoxide compounds. Therefore, the hydrolysis of alkoxy ester is particular performed below 25° C., more particular from 18° C. to 22° C. to have reduced level of dimer compound and sulfoxide compound.

In general, the reaction mixture after hydrolysis of alkoxy ester compound of Formula (VI) may be washed with one or more solvents. The solvent comprises one or more of water, methanol, ethanol, isopropanol, 2-propanol, 1-butanol, t-butyl alcohol, acetone, butanone, methyl isobutyl ketone, ethyl acetate, isopropyl acetate, isobutyl acetate, methyl t-butyl ether, t-butyl acetate, n-butyl acetate, methylene dichloride, ethylene dichloride, and chlorobenzene, or mixture thereof. In particular, the mixture of water and methyl t-butyl ether can be used.

In general, the separated aqueous layer may be treated with one or more organic solvents and pH is adjusted 2.0 to 6.0 with hydrochloride acid solution. The pH, in particular, is adjusted from about 5.0 to 6.0 and the organic layer is separated. In general, the organic solvent comprises one or more of methanol, ethanol, isopropanol, 2-propanol, 1-butanol, t-butyl alcohol, acetone, butanone, methyl isobutyl ketone, ethyl acetate, isopropyl acetate, isobutyl acetate, methyl t-butyl ether, t-butyl acetate, n-butyl acetate, methylene dichloride, ethylene dichloride, and chlorobenzene, or mixture thereof. In particular methyl t-butyl ether can be used.

The separated organic layer may be treated with S-(−)-α-methylbenzyl amine and stirred for 1-3 hours at 10° C.-35° C. to obtain saroglitazar SMBA salt. Particularly for about 2 hours at 20° C. Further, the reaction mass is filtered, washed with one or more solvent and dried to obtain to obtain saroglitazar SMBA salt. The solvent comprises one or more of ethyl acetate, isopropyl acetate, isobutyl acetate, methyl t-butyl ether, t-butyl acetate, n-butyl acetate, methylene dichloride, ethylene dichloride, and chlorobenzene, or mixture thereof. In particular, methyl t-butyl ether can be used.

The saroglitazar SMBA salt may be purified with one or more solvents at 10° C.-30° C. to obtain pure saroglitazar SMBA salt. Particularly for about 2 hours at 20° C. The solvent comprises one or more of water, methanol, ethanol, isopropanol, 2-propanol, 1-butanol, t-butyl alcohol, acetone, butanone, methyl isobutyl ketone, ethyl acetate, isopropyl acetate, isobutyl acetate, methyl t-butyl ether, t-butyl acetate, n-butyl acetate, methylene dichloride, ethylene dichloride, tetrahydrofuran and chlorobenzene, or mixture thereof. In particular mixture of tetrahydrofuran and water may be used. The purification process mentioned above can be repeated to obtain saroglitazar SMBA salt in purer form.

In general, the pure saroglitazar SMBA salt can be treated with one or more solvents. The solvent comprises one or more of water, methanol, ethanol, isopropanol, 2-propanol, 1-butanol, t-butyl alcohol, acetone, butanone, methyl isobutyl ketone, ethyl acetate, isopropyl acetate, isobutyl acetate, t-butyl acetate, n-butyl acetate, methylene dichloride, ethylene dichloride, and chlorobenzene, or mixture thereof. In particular, isopropyl acetate can be used.

The separated aqueous layer may be treated with a magnesium source to obtain saroglitazar magnesium. In general, the magnesium source comprises one or more of magnesium hydroxide, magnesium methoxide, magnesium acetate, magnesium chloride, and magnesium metal. In particular, the magnesium source can be magnesium acetate tetrahydrate in the form of its solution in water.

In general, the reaction mixture thus obtained may be extracted with one or more of solvents. The solvent comprises one or more of ethyl acetate, isopropyl acetate, isobutyl acetate, t-butyl acetate, n-butyl acetate, methylene dichloride, ethylene dichloride, and chlorobenzene, or mixture thereof. In particular, methylene dichloride can be used.

In general, the methylene dichloride may be removed by distillation under vacuum to obtain reaction mass, which is further treated with one or more solvents to obtain substantially pure saroglitazar magnesium. The solvent comprises one or more of water, methanol, ethanol, isopropanol, 2-propanol, 1-butanol, t-butyl alcohol, acetone, butanone, methyl isobutyl ketone, ethyl acetate, isopropyl acetate, isobutyl acetate, t-butyl acetate, n-butyl acetate, methylene dichloride, ethylene dichloride, n-heptane and chlorobenzene, or mixture thereof. In particular, n-butyl acetate and n-heptane can be used.

The product thus obtained may be dried under vacuum tray drier, sieved and milled to obtain suitable particle size range. The milled product may be further dried till constant weight is obtained.

In another general aspect, there is provided a composition comprising saroglitazar magnesium in an amount of about 99.5% or more by weight, and one or more of an aldehyde compound of Formula (II), or a diketo oxirane compound of Formula (III), or a hydroxy methyl compound of Formula (IV), or a dimer compound of Formula (V), each present in an amount of about 0.15%, or less, by weight, when measured by area percentage of HPLC.

TABLE 1

Summary of HPLC analysis of Saroglitazar magnesium

| Sample | HPLC Purity | Aldehyde | Diketo oxirane | Hydroxy methyl | Dimer |
|---|---|---|---|---|---|
| Saroglitazar magnesium | 99.70% | 0.01% | N.D. | N.D. | 0.10% |

N.D. indicates "Not Detected"

In another general aspect, there is provided a stable composition of Saroglitazar magnesium, wherein the composition contains Saroglitazar magnesium having purity of about 99.0% or more, by weight, by area percentage of HPLC, and one or more of the aldehyde compound of Formula (II), the diketo oxirane compound of Formula (III), the hydroxy methyl compound of Formula (IV), or the dimer compound of Formula (V) in an amount of about 0.15%, or less, by weight, relative to saroglitazar magnesium, on prolonged storage and under different stability conditions i.e. 40° C.±2° C. temperature and 75%±5% relative humidity and at 25° C.±2° C. temperature and 60±5% relative humidity as outlined by the six months' stability data as shown in Table-2 and 3.

TABLE 2

Stability data at 40° C. ± 2° C. and 75% ± 5% relative humidity:

| S.No. | Tests | Initial | 1 month | 2 month | 3 months | 6 months |
|---|---|---|---|---|---|---|
| 1. | Description | Off white color | Off white color | Off white color | Off white color | Off white color |
| 2. | LOD(% w/w) | 0.51 | 0.48 | 0.44 | 0.30 | 0.24 |
| 3. | Related Substance by HPLC(% w/w): | | | | | |

TABLE 2-continued

Stability data at 40° C. ± 2° C. and 75% ± 5% relative humidity:

| S.No. | Tests | Initial | 1 month | 2 month | 3 months | 6 months |
|---|---|---|---|---|---|---|
| | i) Formula II | 0.01 | 0.01 | 0.01 | 0.01 | ND |
| | ii) Formula III | N.D. | N.D. | N.D. | N.D. | ND |
| | iii) Formula IV | N.D. | N.D. | N.D. | N.D. | ND |
| | iv) Formula V | 0.11 | 0.12 | 0.12 | 0.11 | 0.12 |
| | Total impurities | 0.18 | 0.12 | 0.12 | 0.12 | 0.12 |

TABLE 3

Stability data at 25° C. ± 2° C. and 60% ± 5% relative humidity:

| S.No. | Tests | Initial | 1 month | 2 month | 3 months | 6 months |
|---|---|---|---|---|---|---|
| 1. | Description | Off white color | Off white color | Off white color | Off white color | Off white color |
| 2. | LOD(% w/w) | 0.51 | 0.43 | 0.64 | 0.27 | 0.35 |
| 3. | Related Substance by HPLC(% w/w): | | | | | |
| | i) Formula II | 0.01 | 0.01 | 0.01 | 0.01 | ND |
| | ii) Formula III | N.D. | N.D. | N.D. | N.D. | ND |
| | iii) Formula IV | N.D. | N.D. | N.D. | N.D. | ND |
| | iv) Formula V | 0.11 | 0.12 | 0.12 | 0.12 | 0.12 |
| | Total impurities | 0.18 | 0.12 | 0.12 | 0.12 | 0.12 |

The purity of the samples of Saroglitazar or salts thereof including magnesium and SMBA salt is measured by area percentage of HPLC using following conditions:
Equipment: Shimadzu LC2020C$_{HT}$ HPLC system or equivalent
Column: YMC-Pack Pro C18 (159 mm×4.0 mm, 3 μm)
Detector: UV-VIS detector or PDA detector
Flow rate: 0.7 mL/min
Wavelength: 294 nm
Injection Vol.: 10 μL
Column Oven Temp.: 25° C.
Run Time: 70 min In another general aspect there is provided a pharmaceutical composition comprising substantially pure Saroglitazar magnesium together with one or more pharmaceutically acceptable excipients, diluents and carriers.

In another general aspect, there is provided a pharmaceutical composition comprising substantially pure Saroglitazar magnesium and aldehyde compound of Formula (II) together with one or more pharmaceutically acceptable excipients, diluents and carriers.

In another general aspect there is provided a pharmaceutical composition comprising substantially pure Saroglitazar magnesium and diketo oxirane compound of Formula (III) together with one or more pharmaceutically acceptable excipients, diluents and carriers.

In another general aspect there is provided a pharmaceutical composition comprising substantially pure Saroglitazar magnesium and hydroxy methyl compound of Formula (IV) together with one or more pharmaceutically acceptable excipients, diluents and carriers.

In another general aspect, there is provided a pharmaceutical composition comprising substantially pure Saroglitazar magnesium and dimer compound of Formula (V) together with one or more pharmaceutically acceptable excipients, diluents and carriers.

In another general aspect, there is provided a pharmaceutical composition comprising substantially pure Saroglitazar magnesium having a mean particle size equal to or less than 100 μm and one or more pharmaceutically acceptable excipients, diluents and carriers.

In general, the pharmaceutical compositions comprising saroglitazar magnesium of the invention may be prepared by using diluents or excipients such as fillers, bulking agents, binders, wetting agents, disintegrating agents, surface active agents, and lubricants. The administration of the pharmaceutical compositions according to the invention may be performed in any of the generally accepted modes of administration available in the art. Illustrative examples of suitable modes of administration include intravenous, oral, nasal, parenteral, topical, transdermal and rectal delivery. Oral delivery is preferred.

The present invention is further illustrated by the following examples.

EXAMPLES

Example-1: Preparation of Alkoxy Ester Compound (Compound of Formula (VI))

In a 5 Liter three necked round bottom flask equipped with nitrogen atmosphere facility, mechanical stirrer, thermometer and an addition funnel, 2-ethoxy-3-(4-hydroxyphenyl)-propionic acid ethyl ester (A) (100.0 g) and cyclohexane (1730.0 ml) were charged and reaction mixture was heated to 45° to 55° C. Potassium carbonate (58.0 g) was added and stirred for 30 min. methane sulfonic acid 2-[2-methyl-5-(4-methylsulfanyl-phenyl)-pyrrol-1-yl]-ethyl ester (A1) (150 g) and tetrahydrofuran (265.0 ml) were added and heated to 75° C. to 85° C. for 48 hours. The reaction mixture was cooled to 25° to 35° C. and water (1000.0 ml) was added and stirred for 15 min. The separated aqueous layer was treated with cyclohexane (200.0 ml) and stirred for 15 min. The organic layers were combined and washed with caustic solution (600.0 ml). The separated organic layer was washed with water (600.0 ml) and characoalized with (5.0 g) charcoal and stirred for 30 min and filtered. The filtrate was distilled to remove cyclohexane and the residue was collected (residue-A).

Example-2: Preparation of Saroglitazar SMBA Salt (Compound of Formula VII)

In a 250 mL three necked round bottom flask equipped with nitrogen atmosphere facility, mechanical stirrer, thermometer and an addition funnel, residue-A obtained in example-1 and ethanol (400 mL) were stirred for 15 min. Sodium hydroxide 20.14 g solution in water (200.0 ml) was added and the reaction mixture was stirred for 3 hours at 18-22° C. methyl tert-butyl ether ("MTBE") (500 mL) was added into reaction mixture and stirred for 20 minutes. The reaction mixture was diluted with water (1800.0 ml) and stirred for 15 min. The separated aqueous layer was washed with MTBE (500 mL). The separated aqueous layer was diluted with MTBE (500 mL) and acidified with conc. HCl at adjust the pH 5-6. The separated aqueous layer was washed with MTBE. The combined organic layer was treated with (S)-(−)-methyl benzyl amine (61 g) and stirred for 1 hour at 25° C. and another one hour at 10-15° C. The reaction mixture was filtered and washed with MTBE. The wet-cake was dried to obtain crude saroglitazar SMBA salt.

Purification of Saroglitazar SMBA Salt

In a 1 Liter three mL three necked round bottom flask equipped with nitrogen atmosphere facility, mechanical stirrer, thermometer and an addition funnel, tetrahydrofuran (125 mL) and saroglitazar SMBA salt (100 g) obtained in example-2 were added at 25° C. and stirred for 15 minutes. The reaction mixture was diluted with water (375 mL)

stirred for 1 hour at 25° C. and another 1 hour at 10-15° C. The reaction mixture was filtered and washed with water. The wet-cake was dried to obtain pure saroglitazar SMBA salt. Repeat the second purification of saroglitazar SMBA salt using the same process mention above.

Example-3: Preparation of Saroglitazar Magnesium (Compound of Formula (I) from Saroglitazar SMBA Salt In a 250 mL three necked round bottom flask equipped with nitrogen atmosphere facility, mechanical stirrer, thermometer and an addition funnel, saroglitazar SMBA obtained in example-2 (100 g) and isopropyl acetate (400 mL) were added at 25° C. The reaction mixture was diluted with water (250 ml) and acidified with conc. HCl at adjust the pH 2-3 and stirred for 15 minutes at 25° C. The organic layer was washed with brine solution and stirred for 15 min. The separated organic layer was treated with water and NaOH solution and stirred for 15 minutes at 25° C. The separated aqueous layer was treated with magnesium acetate tetrahydrate (38.3 g) in water (100 mL) solution and stirred for 60 min. The reaction mixture was extracted with methylene dichloride (400 mL). The separated organic layer was washed with brine solution and stirred for 15 minutes at 25° C. The separated lower organic layer was treated with magnesium sulfate. The mixture was filtered and washed with MDC. N-butyl acetate was added to filtrate then MDC was distilled out under vacuum below 40° C. The reaction mass was diluted with n-butyl acetate (30 ml). In n-heptane (900 mL), diluted reaction mass was added and stirred for 1 hour. The product was filtered and washed with n-heptane and dried in vacuum tray dryer at 25° C. to 35° C. for 3 hours. The product was sieved through 0.5 mm sieve and milled through jet-milled. The product was further dried in vacuum tray drier at 35° C. to 45° C. for 3 hours followed by drying at 55° C. to 65° C. at 12 hours to obtain substantially amorphous saroglitazar magnesium (I). HPLC Purity: 99.87%.

Example 4: Preparation of Compound of Formula (3A)

In a 2000 mL three necked round bottom flask was added solution of compound of Formula (1A) 100 g in toluene (800 mL).TBAB (10 g) was added to the reaction mixture and the reaction mass was cooled to 15-20° C. Potassium hydroxide (134 g) was added in two portions of equal size. After addition of one portion the reaction mass was stirred and diethyl sulphate (142 g) was added and the reaction was stirred for 30 minutes and then section portion was added followed by addition of diethyl sulphate (142 g). Reaction mass was stirred for 8 hours and then water was added to the reaction mixture and the temperature was lowered to 5 to 15° C. Layers separation was done at 5 to 15° C. and then the organic layer was collected and the solvent distilled out under vacuum. To the residue obtained was added water (400 mL) and triethyl amine (204.4 g) at 25-35° C. Heat the reaction mass to 60-70° C. and stir for 4 hours. Cool the reaction mass and then toluene was added followed by layer separation. The organic layer was then distilled under vacuum to obtain oily residue. Diethyl sulphate content: <0.01%.

To the oily residue obtained was added ethanol (600 mL), triethyl amine (4 mL) and 10% Pd/C (3.0 g) at a pressure of 5 kg/cm² at a temperature of 40-45° C. in an autoclave. Stir for 2 hours and then cool to 25-30° C. and then add Pd/C (0.3 g) and then heat to 40-45° C. Stir for two hours and then filter the reaction mass and distill out the solvent under vacuum. Crystallize from diisopropyl ether and heptane. Dry the solids under vacuum in oven. Weight: 64 g and Yield: Approx 0.86%.

Example 5: Preparation of Compound of Formula (2B)

In a 2000 mL three necked round bottom flask was added toluene solution containing compound of Formula (1B) and triethyl amine (39.70 g). The reaction mixture was cooled to 10 to 20° C. Methane sulphonyl chloride was added to the reaction mixture over a period of time. The reaction mass was stirred for one hour and to it was added water (400 mL) and the reaction was further cooled to 0 to 5° C. and stirred for 3 hours. The obtained solids were filtered and dried in oven under vacuum. Yield: 90% and HPLC purity: 99.80% and dimer of mesylate compound 0.08%.

While the present invention has been described in terms of its specific embodiments, certain modifications and equivalents will be apparent to those skilled in the art and are intended to be included within the scope of the present invention.

We claim:

1. A composition comprising saroglitazar magnesium having a purity of about 99.0% or more by weight, and one or more of an aldehyde compound of Formula (II), a diketo oxirane compound of Formula (III), and a hydroxy methyl compound of Formula (IV), each of the compounds of Formula (II), Formula (III), or Formula (IV), when present, is in a detectable amount of about 0.15% or less, relative to saroglitazar magnesium by weight, when measured by area percentage of HPLC,

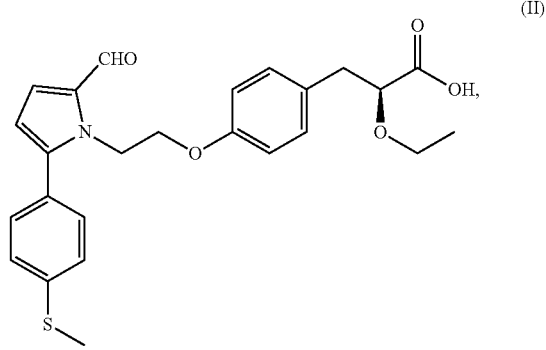 [SMILES: CCO[C@@H](Cc1ccc(OCCn2c(C=O)ccc2-c2ccc(SC)cc2)cc1)C(=O)O]

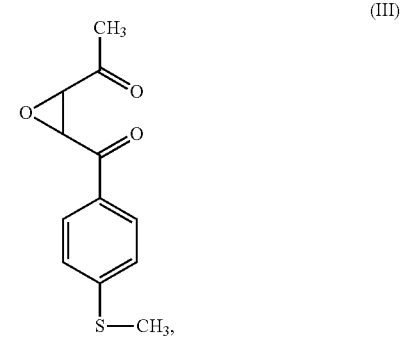 [SMILES: CSc1ccc(C(=O)C2OC2C(C)=O)cc1]

-continued

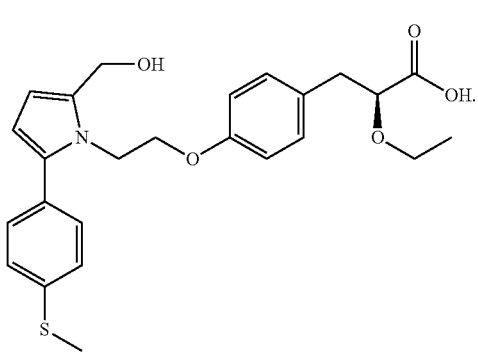
(IV)

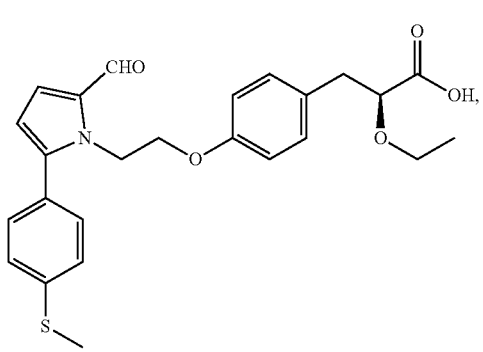
(II)

2. The composition according to claim 1, wherein the composition comprises saroglitazar magnesium having a purity of about 99.5% or more by weight, and one or more of the aldehyde compound of Formula (II), the diketo oxirane compound of Formula (III), or the hydroxy methyl compound of Formula (IV), each of the compound of Formula (II), Formula (III), or Formula (IV), when present, is in a detectable amount of about 0.15% or less, relative to saroglitazar magnesium by weight, when measured by area percentage of HPLC.

3. The composition according to claim 1, wherein the composition comprises saroglitazar magnesium having a purity of about 99.0% or more by weight, and the aldehyde compound of Formula (II) is present in a detectable amount of about 0.15% or less, relative to saroglitazar magnesium by weight, when measured by area percentage of HPLC.

4. The composition according to claim 1, wherein the composition comprises saroglitazar magnesium having a purity of about 99.0% or more by weight, and the diketo oxirane compound of Formula (III) is present in a detectable amount of about 0.15% or less, relative to saroglitazar magnesium by weight, when measured by area percentage of HPLC.

5. The composition according to claim 1, wherein the composition comprises saroglitazar magnesium having a purity of about 99.0% or more by weight, and the hydroxy methyl compound of Formula (IV) is present in a detectable amount of about 0.15% or less, relative to saroglitazar magnesium by weight, when measured by area percentage of HPLC.

6. The composition according to claim 1, wherein the aldehyde compound of Formula (II), the diketo oxirane compound of Formula (III), and the hydroxy methyl compound of Formula (IV), each of the compounds of Formula (II), Formula (III), or Formula (IV), when present, is in a detectable amount of about 0.15%, or less by weight, relative to saroglitazar magnesium, after storage for 6 months at 40° C.±2° C. temperature and 75% ±5% relative humidity, or at 25° C.±2° C. temperature and 60% ±5% relative humidity, when measured by area percentage of HPLC.

7. A compound selected from an aldehyde compound of Formula (II), a diketo oxirane compound of Formula (III), and a hydroxymethyl compound of Formula (IV),

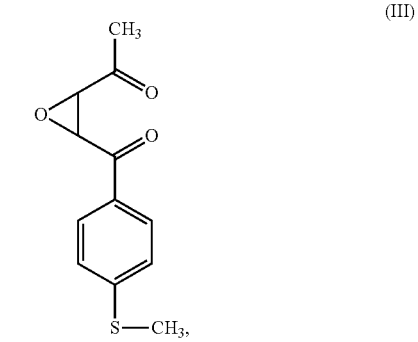 [SMILES: CSc1ccc(C(=O)C2OC2C(C)=O)cc1]
(III)

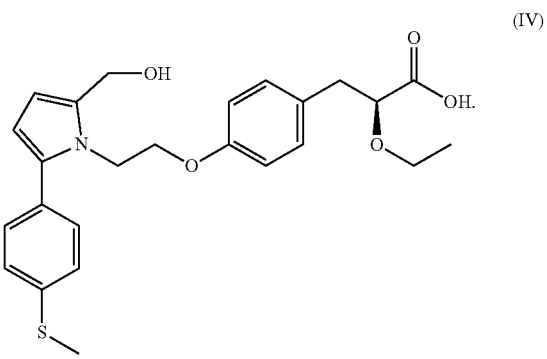
(IV)

8. A process for the preparation of the substantially pure saroglitazar magnesium, wherein the process comprises:
(a) reacting a hydroxy compound (3A) with a mesylate compound (2B) in a one or more solvents in the presence of a base to obtain an alkoxy ester compound of Formula (VI);

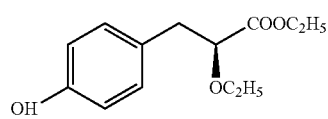
(3A)

-continued (2B)

(VI)

(b) hydrolyzing the alkoxy ester compound of Formula (VI) with a base in one or more solvents at a temperature below 25° C. to obtain a reaction mixture;
(c) adjusting pH of the reaction mixture to 2.0 to 6.0;
(d) extracting the reaction mixture with one or more organic solvents to obtain an organic layer;
(e) treating the organic layer with S-(−)-α-methylbenzyl amine to obtain saroglitazar S-(−)-α-methylbenzyl amine (SMBA) salt of Formula (VII);

(VII)

(f) purifying the saroglitazar SMBA salt with one or more solvents to obtain pure saroglitazar SMBA salt; and
treating the pure saroglitazar SMBA salt with magnesium source to obtain the composition comprising substantially pure saroglitazar magnesium.

9. The process according to claim 8, wherein the reaction mixture at step (b) is washed with one or more organic solvents to obtain an aqueous layer and adjusting the pH of the aqueous layer to 2.0 to 6.0.

10. The process according to claim 8, wherein the solvent at step (a) is one or more of alcohols selected from methanol, ethanol, isopropanol, 2-propanol, 1-butanol, and t-butyl alcohol; ketones selected from acetone, butanone, and methyl isobutyl ketone; esters selected from ethyl acetate, isopropyl acetate, t-butyl acetate, and isobutyl acetate; chlorinated hydrocarbons selected from methylene dichloride, ethylene dichloride, and chlorobenzene;
hydrocarbons selected from pentane, hexane, heptane, and cyclohexane; ethers selected from tetrahydrofuran, 1,4-dioxane, diisopropyl ether, diethyl ether, and methyl tert-butyl ether; or mixture thereof.

11. A composition comprising saroglitazar magnesium, wherein the saroglitazar magnesium is present in an amount of about 99.0% or more by weight, by area percentage of HPLC, and one or more of an aldehyde compound of Formula (II), a diketo oxirane compound of Formula (III), and a hydroxy methyl compound of Formula (IV), each of the compounds of Formula (II), Formula (III), or Formula (IV), when present, is in a detectable amount of about 0.15% or less by weight, relative to saroglitazar magnesium, by area percentage of HPLC, after storage for 6 months at 40° C.±2° C. temperature and 75% ±5% relative humidity or at 25° C.±2° C. temperature and 60±5% relative humidity, (II)

(III)

(IV)

12. A pharmaceutical composition comprising saroglitazar magnesium having a purity of about 99.0% or more by weight, and one or more of an aldehyde compound of Formula (II), a diketo oxirane compound of Formula (III), and a hydroxy methyl compound of Formula (IV), each of the compounds of Formula (II), Formula (III), or Formula (IV), when present, is in a detectable amount of about 0.15% or less, relative to saroglitazar magnesium by weight, when measured by area percentage of HPLC, together with pharmaceutically acceptable excipients, diluents and carriers,

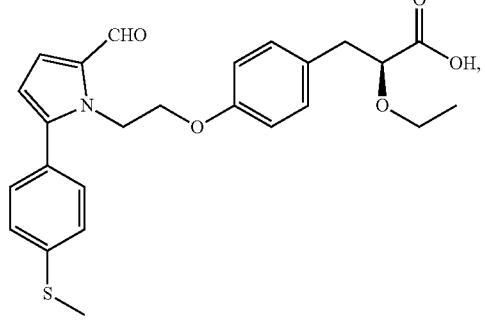

(II)

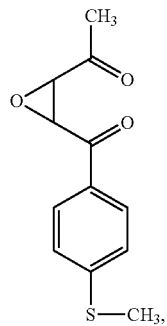

(III)

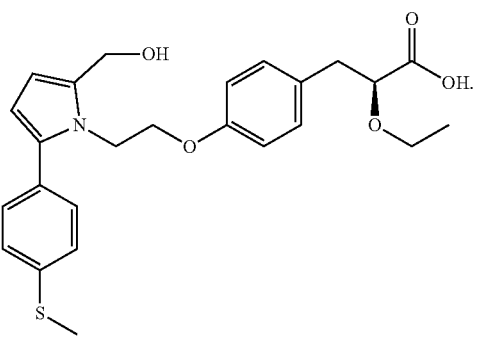

(IV)

* * * * *